United States Patent
Hasenzahl

(10) Patent No.: US 6,896,859 B2
(45) Date of Patent: May 24, 2005

(54) METHOD FOR THE PRODUCTION OF A TITANIUM-CONTAINING ZEOLITE

(75) Inventor: Steffen Hasenzahl, Maintal (DE)

(73) Assignee: Degussa AG, Düsseldorf (DE)

( * ) Notice: Subject to any disclaimer, the term of this patent is extended or adjusted under 35 U.S.C. 154(b) by 108 days.

(21) Appl. No.: 10/220,454

(22) PCT Filed: Feb. 24, 2001

(86) PCT No.: PCT/EP01/02119

§ 371 (c)(1),
(2), (4) Date: Aug. 29, 2002

(87) PCT Pub. No.: WO01/64582

PCT Pub. Date: Sep. 7, 2001

(65) Prior Publication Data

US 2003/0035771 A1 Feb. 20, 2003

(30) Foreign Application Priority Data

Mar. 2, 2000 (EP) .............................................. 00104325

(51) Int. Cl.$^7$ ........................ C01B 33/20; C07B 301/12; B01J 29/89
(52) U.S. Cl. ............... 423/326; 423/705; 423/DIG. 22; 585/531
(58) Field of Search ................................ 423/326, 705, 423/DIG. 22; 549/531

(56) References Cited

U.S. PATENT DOCUMENTS

| | | | |
|---|---|---|---|
| 4,954,653 A | * | 9/1990 | Bellussi et al. ............. 564/223 |
| 5,525,563 A | | 6/1996 | Thiele et al. |
| 5,637,715 A | | 6/1997 | Thiele et al. |
| 5,756,778 A | | 5/1998 | Thiele et al. |
| 5,885,546 A | | 3/1999 | Kumar et al. |
| 5,919,430 A | | 7/1999 | Hasenzahl et al. |
| 6,054,112 A | | 4/2000 | Hasenzahl et al. |
| 6,106,803 A | | 8/2000 | Hasenzahl et al. |
| 6,387,349 B1 | * | 5/2002 | Kulkarni et al. ............. 423/707 |

FOREIGN PATENT DOCUMENTS

| | | |
|---|---|---|
| BE | 1001038 | 3/1990 |
| DE | 196 23 611 | 12/1997 |
| DE | 196 23 972 | 12/1997 |
| DE | 198 39 792 | 3/2000 |
| EP | 0 325 053 | 7/1989 |
| EP | 0 791 558 | 8/1997 |
| EP | 0 906 784 A2 | 4/1999 |
| EP | 0 906 784 A3 | 3/2000 |
| FR | 2 471 950 | 6/1981 |
| JP | 02298350 A * | 12/1990 |
| WO | WO 99/28030 | 6/1999 |
| WO | WO 99/52626 | 10/1999 |

OTHER PUBLICATIONS

Zhang, G. et al., "Preparation Of Colloidal Suspensions Of Discrete Ts–1 Crystals," Chemistry of Materials, 1997, pp. 210–217, vol. 9, No. 1, American Chemical Society, Washington, D.C., USA , 8 pps.

A. Thangaraj, et al., "*Studies on the synthesis of titanium silicalite, TS–1*", Zeolites, 1992, vol. 12, Nov./Dec., pp. 943–950.

A. Thangaraj, et al., "*Catalytic Properties of Crystalline Titanium Silicalites*", National Chemical Laboratory, Pune–411 008, India, Journal of Catalysis 130, 1–8 (1001).

* cited by examiner

Primary Examiner—David Sample
(74) Attorney, Agent, or Firm—Smith, Gambrell & Russell, LLP

(57) ABSTRACT

The present invention concerns a method for the production of a titanium-containing zeolite by: (a) combining a hydrolyzable silicon compound and a hydrolyzable titanium compound; (b) adding a basic quaternary ammonium compound in an aqueous medium to the mixture from (a) and hydrolysing the reaction mixture at a temperature in the range from 0° C. to 100° C. to form a synthesis sol; then (c) heating the synthesis sol to a temperature in the range from 150° C. to 190° C.; and (d) crystallizing the synthesis sol at this temperature, characterized in that the heating-up time in step (c) is less than 240 min.

12 Claims, No Drawings

METHOD FOR THE PRODUCTION OF A TITANIUM-CONTAINING ZEOLITE

The present invention concerns a method for the production of a titanium-containing zeolite and the use of a zeolite obtainable in this way as a catalyst for the epoxidation of olefins with hydrogen peroxide and a method for the epoxidation of olefins in the presence of a titanium-containing zeolite produced by the method according to the invention.

A method for the production of titanium silicalite and also the use of the titanium silicalite thus produced as a catalyst in a series of reactions, among them oxidation reactions, is known from U.S. Pat. No. 4,410,501. It describes two different procedures, including the formation of a synthesis gel starting from a hydrolyzable silicon compound such as tetraethyl orthosilicate, for example, and a hydrolyzable titanium compound by the addition of tetra-n-propyl ammonium hydroxide (TPAOH) and hydrolysis of this reaction mixture.

In subsequent years many groups of researchers in industry and universities have sought to optimize the synthesis of titanium silicalite, in terms of both the activity of the resulting catalyst and the efficiency of the method, starting from the teaching of U.S. Pat. No. 4,410,501.

Thus the influence of a number of process parameters such as, e.g., type of $SiO_2$ source, crystallization time, crystallization conditions, ratio of template compound/silicon and silicon/titanium in the starting materials on the activity of the resulting catalyst, has been investigated in various scientific publications (A. J. H. van der Pol and J. H. C. van Hooff, Applied Catalysis A: General, 92 (1992) 93–100; van der Pol, Verduyn and van Hooff, Applied Catalysis A: General, 92 (1992) 113–130; J. A. Martens et al., Applied Catalysis A: General, 93 (1993) 71–84). Nevertheless, despite a very extensive and detailed examination of the parameters that influence the synthesis and activity of titanium silicalite catalysts, there is still a need within the industry to further improve the production method in terms of the activity of the resulting catalyst.

The object of the present invention is therefore to further improve the synthesis of titanium-containing zeolites starting from the prior art described above, in order to increase the activity of the resulting catalyst, particularly for the epoxidation of olefins.

This object is achieved by a method for the production of a titanium-containing zeolite by
  a) combining a hydrolyzable silicon compound and a hydrolyzable titanium compound,
  b) adding a basic quaternary ammonium compound in an aqueous medium to the mixture from a) and hydrolysing the reaction mixture at a temperature in the range from 0° C. to 100° C. to form a synthesis sol, then
  c) heating the synthesis sol to a temperature in the range from 150° C. to 190° C.,
  d) crystallizing the synthesis sol at this temperature, characterized in that the heating-up time in step c) is less than 240 min.

According to a preferred embodiment, the heating-up time in step c) is between 60 and 180 min, preferably between 80 and 150 min, with a heating-up time of 90 to 120 min being most preferred.

According to the present invention a hydrolyzable silicon compound and a hydrolyzable titanium compound are first hydrolyzed with a basic quaternary ammonium compound in the presence of water. Particularly suitable as hydrolyzable silicon or titanium compounds for the method according to the invention are the tetraalkyl orthosilicates or tetraalkyl orthotitanates, whereby alkyl is preferably selected from the group consisting of methyl, ethyl, propyl or butyl. The most preferred starting compounds are tetraethyl orthosilicate and tetraethyl orthotitanate, whereby alkyl is preferably selected from the group consisting of methyl, ethyl, propyl or butyl. The most preferred starting compounds are tetraethyl orthosilicate and tetraethyl orthotitanate.

The quaternary ammonium compound is a template compound that determines the crystal structure by absorption in the crystal lattice of the product during crystallization. Tetraalkyl ammonium compounds such as tetraalkyl ammonium hydroxide, particularly tetra-n-propyl ammonium hydroxide, are preferably used to produce titanium silicalite-1 (MFI structure), tetra-n-butyl ammonium hydroxide to produce titanium silicalite-2 (MEL structure) and tetraethyl ammonium hydroxide to produce titanium-β-zeolite (BEA crystal structure) The quaternary ammonium compound is preferably used as an aqueous solution.

The pH value for the synthesis sol of >9, preferably >11, that is necessary for synthesis is adjusted by the basic-reacting quaternary ammonium compound.

The temperature at which the synthesis sol is produced can be selected between broad limits, but the mixture of hydrolyzable silicon compound and hydrolyzable titanium compound is preferably cooled to a temperature in the range from 0° C. to 10° C., preferably 0° C. to 5° C., particularly preferably 1° C. and the basic quaternary ammonium compound is then added in an aqueous solution cooled to the same temperature.

In a further embodiment of the present invention, where tetraalkyl orthosilicates and tetraalkyl orthotitanates are used as silicon or titanium source respectively, after step b) and before step c) of the method according to the invention the synthesis sol is heated to a temperature of 75° C. to 95° C. for a period of 120 to 200 min and the resulting alcohol distilled off as a water azeotrope in order to support the hydrolysis of the titanium and silicon compound. Conventionally the volume of alcohol/water azeotrope removed by distillation is replaced in the reaction mixture at least in part by water in order to avoid the formation of a solid gel or of wall deposits during crystallization.

The synthesis sol produced at the end of hydrolysis is then heated to the crystallization temperature of 150° C. to 190° C. over a further period defined above. Surprisingly it has been found that the activity of the resulting catalyst depends on the heating-up time in which the synthesis sol is heated to the crystallization temperature.

Under the specified conditions of the method according to the invention, the crystallization time is conventionally less than 3 days, preferably a maximum of 24 hours. The crystals are separated from the parent liquor by filtration, centrifugation or decantation and washed with a suitable washing liquid, preferably water. The crystals are then optionally dried and calcined at a temperature of between 400° C. and 1000° C., preferably between 500° C. and 750° C., to remove the template.

The crystalline titanium-containing zeolites according to the invention are obtained in powder form. For their use as oxidation catalysts they can optionally be converted into a suitable shape for use, such as, for example, micro-pellets, balls, tablets, solid cylinders, hollow cylinders or honeycomb shapes, by known methods for shaping powdered catalysts such as. for example, pelletisation, spray drying, spray pelletisation or extrusion.

The titanium-containing zeolite produced according to the invention can be used as a catalyst in oxidation reactions with $H_2O_2$. In particular the titanium-containing zeolite according to the invention can be used as a catalyst in the epoxidation of olefins by means of aqueous hydrogen peroxide in a solvent miscible with water.

Using the method according to the invention, the activity of the titanium-containing zeolites produced according to the invention can be further improved by relatively simple means, particularly in epoxidation reactions of olefins.

The present invention is illustrated in greater detail by means of the examples.

EXAMPLE 1

3,415.2 g tetraethyl orthosilicate are placed in a 10 l autoclave rendered inert with nitrogen, 93.5 g tetraethyl orthotitanate are added with stirring and the resulting mixture is cooled to approx. 1.0° C. A solution consisting of 1,417 g tetra-n-propyl ammonium hydroxide (TPAOH, 40 wt. % solution) and 3.075 g deionised water is then added with stirring at this temperature over around 5 hours by means of a hose pump. In order to complete the hydrolysis and to distil off the ethanol formed, the reaction mixture was heated first to approx. 80° C. and then to max. 95° C. over around 3 hours. The ethanol-water azeotrope distilled off in this way is replaced by the same volume of deionised water.

The synthesis sol was then heated over 150 min to 175° C. and kept at this temperature for a period of 120 min. After cooling of the resulting titanium silicalite-1 suspension, the solid formed was separated by centrifugation from the strongly basic parent liquor still containing TPAOH, washed, dried overnight at 120° C. and then calcined in air at 550° C. for 5 hours in a muffle furnace.

The product properties such as titanium content in the resulting titanium silicalite and the activity coefficient are set out in Table 1.

The activity coefficient was measured as follows:

1.0 g of the titanium silicalite catalyst produced in example 1 in 300 ml methanol was then placed in a thermostatically controlled laboratory autoclave with aeration stirrer at 40° C. under a propylene atmosphere and the solvent saturated with propylene at 3 bar overpressure. 13.1 g of 30 wt. % aqueous hydrogen peroxide solution are then added in one portion and the reaction mixture kept at 40° C. and 3 bar, with propylene being made up via a pressure regulator to compensate for consumption by the reaction. Samples were taken at regular intervals via a filter and the hydrogen peroxide content of the reaction mixture determined by redox titration with cerium(IV) sulfate solution. Plotting $\ln(c/c_0)$ against time t, where c is the $H_2O_2$ concentration measured at time t and $c_0$ is the $H_2O_2$ concentration calculated at the start of the reaction, produces a straight line. The activity coefficient was determined from the gradient of the straight line using the equation $$\frac{dc}{dt} = k \cdot c \cdot c_{cat}$$

where $c_{cat}$ stands for the catalyst concentration in kg catalyst per kg reaction mixture.

EXAMPLES 2 AND 3

Example 1 was repeated with identical molar ratios of the starting compound. Only the batch size and heating-up time were varied. Batch size, heating-up time and product properties of the resulting titanium silicalite catalyst are set out in Table 1.

Comparative Example 1

128.1 kg tetraethyl orthosilicate were placed in a dry 300 l reactor with distillation column rendered inert with nitrogen and 3.51 kg tetraethyl orthotitanate were added with stirring. The reactor contents were cooled to 0° C. by rinsing with nitrogen. A mixture of 53.12 kg tetra-n-propyl ammonium hydroxide solution (TPAOH, 40 wt. % solution) and 100 kg deionised water was then added over 6.5 hours. In order to complete the hydrolysis, the reaction mixture was heated first to 77° C. and then to 96° C. over 5.5 hours. The ethanol/water azeotrope distilled off in the process was replaced by the same volume of deionised water. The synthesis sol was then pumped into a 300 l autoclave, heated to 175° C. over 8 hours with stirring and kept at this temperature for 1 hour. After cooling of the resulting titanium silicalite suspension it was processed as described in example 1.

The main process parameters and the properties of the resulting product are set out in Table 1.

Comparative Experiments 2 and 3

Comparative experiments 2 and 3 were performed in the same way as comparative experiment 1 with identical molar ratio of the starting compound. Only the batch size and heating-up time were as set out in Table 1. The properties of the resulting titanium silicalite products are also summarised in Table 1.

TABLE 1

|  |  |  | Product properties | |
|---|---|---|---|---|
| Example | Batch size (l) | Heating-up time (h) | Titanium content (wt. % $TiO_2$) | Activity coefficient ($min^{-1}$) |
| 1 | 10 | 2.5 | 2.8 | 30.5 |
| 2 | 1 | 1.5 | 3.2 | 31.6 |
| 3[a] | 1 | 1.5 | 2.9 | 30.8 |
| 4[b] | 1 | 2.5 | 3.0 | nd |
| C1 | 300 | 8 | 2.5 | 26.9 |
| C2 | 300 | 8 | 2.4 | 22.5 |
| C3[b] | 1 | 8 | 2.5 | 22.4 |

[a] Synthesis sol produced on a 300 l scale.
[b] Synthesis sol produced on a 2 l scale and then divided.

The primary crystallite size of the titanium silicalites produced according to the examples in accordance with the present invention and according to the comparative examples are in the range from 0.3 to 0.4 μm, regardless of the batch size and heating-up time.

If the examples according to the present invention are compared with the comparative examples, it can be seen that the heating-up time has a direct influence on the activity of the resulting catalyst. Without wishing to commit to a theory, it is clear from the experimental results that the increase in the content of the titanium incorporated into the crystal lattice correlates to the reducing heating-up time. This correlation could be a reason for the increase in catalyst activity that was surprisingly found as the time over which the synthesis sol is brought to crystallisation temperature is reduced.

What is claimed is:

1. Method for the production of a titanium-containing zeolite comprising
   a) combining a hydrolyzable silicon compound and a hydrolyzable titanium compound,
   b) adding a basic quaternary ammonium compound in an aqueous medium to the mixture from a) and hydrolysing the reaction mixture at a temperature in the range from 0° C. to 100° C. to form a synthesis sol, then c) heating the synthesis sol to a temperature in the range from 150° C. to 190° C. and d) crystallizing the synthesis sol at this temperature.

characterized in that the heating-up time in step c) is less than 240 minutes.

2. Method according to claim 1, characterized in that the heating-up time in stop c) is 60 to 180 minutes.

3. Method according to claim 1, characterized in at the hydrolyzable silicon compound is a tetraalkyl orthosilicate, and the hydrolyzable titanium compound is a tetraalkyl orthotitanate.

4. Method according to claim 3, characterized in that after step b) and before step c) the synthesis sol is heated to a temperature of 75° C. to 100° C. for a period of 120 to 200 minutes and the resulting alcohol is distilled off in order to support the hydrolysis of the hydrolyzable titanium and silicon compounds and optionally the volume of alcohol removed by distillation is replaced at least in part by the addition of water to the synthesis sol.

5. Method according to claim 1, whereby the quaternary ammonium compound is a tetraalkyl ammonium hydroxide.

6. Method according to claim 1, wherein the heating-up time in step c) is 80 to 120 minutes.

7. Method according to claim 1, wherein the hydrolyzable silicon compound is a tetraethyl orthosilicate, and the hydrolyzable titanium compound is a tetraalkyl orthotitanate.

8. Method according to claim 1, wherein the quaternary ammonium compound is a tetra-n-propyl ammonium hydroxide.

9. Method according to claim 1, whereby the titanium-containing zeolitic is separated off, dried and calcined.

10. Method for the epoxidation of olefins by reacting olefins with aqueous hydrogen peroxide in a solvent miscible with water in the presence of a titanium-containing zeolite as a catalyst that is obtained by the method according to claim 9.

11. Method for the epoxidation of olefins by reacting olefins with hydrogen peroxide in the presence of titanium-containing zeolite as catalyst obtained by the method according to claim 9.

12. Method for the epoxidation of olefins comprising reacting olefins with aqueous hydrogen peroxide in a solvent miscible with water in the presence of a titanium-containing zeolite as catalyst which is obtained by a) combining a hydrolyzable silicon compound and a hydrolyzable titanium-containing compound b) adding a basic quaternary ammonium compound in an aqueous medium to the mixture from a) and hydrolyzing the reaction mixture at a temperature in the range of from 0° C. to 100° C. to obtain a synthesis sol, c) heating the synthesis sol to a temperature in the range of from 150 to 190° C., crystallizing the synthesis sol at 150° C. to 190° C., separating off the titanium-containing zeolite thereby prepared, drying and calcining said zeolite wherein heating up time in c) is less than 240 minutes.

* * * * *

UNITED STATES PATENT AND TRADEMARK OFFICE
CERTIFICATE OF CORRECTION

PATENT NO. : 6,896,859 B2
APPLICATION NO. : 10/220454
DATED : May 24, 2005
INVENTOR(S) : Hasenzahl, Steffen It is certified that error appears in the above-identified patent and that said Letters Patent is hereby corrected as shown below:

Column 5,
Line 3, should read as follows:
-- d) crystallizing the synthesis sol at this temperature, --.
Line 7, should read as follows:
-- characterized in that the heating-up time in step c) is 60 --.
Line 9, should read as follows:
-- 3. Method according to claim 1, characterized in that the --.
Line 27, should read as follows:
-- lyzable titanium compound is a tetraethyl orthotitanate. --.

Column 6,
Line 2, should read as follows:
-- containing zeolite is separated off, dried and calcined. --.
Line 17, should read as follows:
-- hydrolyzable titanium-containing compound, --.
Lines 24-27, should read as follows:
-- d) crystallizing the synthesis sol at 150°C. to 190°C., separating off the titanium-
    containing zeolite thereby prepared, drying and calcining said zeolite,
wherein the heating-up time in c) is less than 240 minutes. --.

Signed and Sealed this

Eleventh Day of July, 2006

JON W. DUDAS
*Director of the United States Patent and Trademark Office*